US012678429B2

(12) United States Patent
Endo

(10) Patent No.: US 12,678,429 B2
(45) Date of Patent: Jul. 14, 2026

(54) PYRIDYLAMINOACETIC ACID COMPOUND AND POLYOXYETHYLENE CASTOR OIL-CONTAINING PHARMACEUTICAL COMPOSITION

(71) Applicant: Santen Pharmaceutical Co., Ltd., Osaka (JP)

(72) Inventor: Yoko Endo, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 18/363,961

(22) Filed: Aug. 2, 2023

(65) Prior Publication Data

US 2023/0372316 A1 Nov. 23, 2023

Related U.S. Application Data

(63) Continuation of application No. 16/711,706, filed on Dec. 12, 2019, now abandoned, which is a continuation of application No. 15/204,475, filed on Jul. 7, 2016, now abandoned, which is a continuation of application No. PCT/JP2015/050333, filed on Jan. 8, 2015.

(30) Foreign Application Priority Data

Jan. 10, 2014 (JP) ................................ 2014-002809

(51) Int. Cl.

| | |
|---|---|
| ***A61K 31/444*** | (2006.01) |
| ***A61K 9/00*** | (2006.01) |
| ***A61K 9/08*** | (2006.01) |
| ***A61K 47/02*** | (2006.01) |
| ***A61K 47/12*** | (2006.01) |
| ***A61K 47/18*** | (2017.01) |
| ***A61K 47/44*** | (2017.01) |

(52) U.S. Cl.

CPC .......... *A61K 31/444* (2013.01); *A61K 9/0048* (2013.01); *A61K 9/08* (2013.01); *A61K 47/02* (2013.01); *A61K 47/12* (2013.01); *A61K 47/183* (2013.01); *A61K 47/44* (2013.01); *Y02A 50/30* (2018.01)

(58) Field of Classification Search

CPC .................................................. A61K 31/444

See application file for complete search history.

(56) References Cited

U.S. PATENT DOCUMENTS

| | | | | |
|---|---|---|---|---|
| 4,960,799 A | 10/1990 | Nagy | | |
| 5,631,287 A | 5/1997 | Schneider et al. | | |
| 5,998,488 A | 12/1999 | Shinohara et al. | | |
| 6,235,781 B1 | 5/2001 | Weiner et al. | | |
| 8,685,986 B2 | 4/2014 | Hagihara et al. | | |
| 9,415,038 B2 * | 8/2016 | Shams | A61P 27/02 | |
| 10,149,908 B2 | 12/2018 | Endo | | |
| 10,485,872 B2 * | 11/2019 | Endo | A61K 47/183 | |
| RE48,183 E * | 9/2020 | Shams | A61K 9/0048 | |
| 10,765,750 B2 * | 9/2020 | Endo | A61K 31/444 | |
| 10,940,144 B2 | 3/2021 | Taniguchi et al. | | |
| 2002/0009507 A1 | 1/2002 | Weimer et al. | | |
| 2002/0165254 A1 | 11/2002 | Kis et al. | | |
| 2011/0054172 A1 | 3/2011 | Iwamura et al. | | |
| 2012/0190852 A1 * | 7/2012 | Hagihara | A61P 27/02 | 546/261 |
| 2012/0263803 A1 | 10/2012 | Mashima et al. | | |
| 2013/0331458 A1 | 12/2013 | Miyano et al. | | |
| 2014/0018350 A1 * | 1/2014 | Kirihara | A61K 9/0048 | 514/218 |
| 2014/0018396 A1 | 1/2014 | Kirihara et al. | | |
| 2015/0072951 A1 | 3/2015 | Sakatani et al. | | |
| 2015/0196541 A1 | 7/2015 | Shams et al. | | |
| 2016/0317512 A1 | 11/2016 | Endo | | |
| 2016/0317664 A1 | 11/2016 | Endo | | |
| 2016/0324838 A1 | 11/2016 | Shams et al. | | |

(Continued)

FOREIGN PATENT DOCUMENTS

| | | |
|---|---|---|
| CA | 2878370 A1 | 1/2014 |
| CA | 2934612 A1 | 7/2015 |

(Continued)

OTHER PUBLICATIONS

Polyoxyl Castor Oil Polyoxyl Hydrogenated Castor Oil, Summary Report, The European Agency for the Evaluation of Medicinal Products, EMEA/MRL/614/99-FINAL, Jun. 1999, available at https://www.ema.europa.eu/en/documents/mrl-report/polyoxyl-castor-oil-polyoxyl-hydrogenated-castor-oil-summary-report-committee-veterina.*

Packaging of Ophthalmic and parenteral products, published on Mar. 29, 2012, available in its entirety at https://www.slideshare.net/Abir420/packaging-of-ophthalmic-and-parenteral-products.*

Packaging of Ophthalmic and parenteral products, Published on Mar. 29, 2012; available in its entirety at https://www.slideshare.net/abir420/packaging-of-ophalmic-and-parenteral-products.

CA Office Action for corresponding CA Application No. 2,935,055, dated Dec. 2, 2020.

CNIPA Office Action for corresponding CN Application No. 20150003056.5, Mailing date of Jun. 16, 2017.

CNIPA Office Action for corresponding CN Application No. 201580003108.9; Mailing Date, Aug. 4, 2017.

CNIPA First Office Action for corresponding CN Application No. 201910493497.8; Mailed on Dec. 16, 2021.

(Continued)

*Primary Examiner* — Svetlana M Ivanova

(74) *Attorney, Agent, or Firm* — CANTOR COLBURN LLP

(57) ABSTRACT

The purpose of the present invention is to provide: a pharmaceutical composition that comprises the pyridylaminoacetic acid compound of the present invention, said pyridylaminoacetic acid compound being stable within the pharmaceutical composition; and a method for improving the stability of the pydridylaminoacetic acid compound within the pharmaceutical composition. The pharmaceutical composition comprises: (6{[4-(pyrazol-1-yl)benzyl](pyridine-3-ylsulfonyl)aminomethyl}pyridine-2-ylamino)isopropyl acetate or a salt thereof; and polyoxyethylene castor oil. The polyoxyethylene castor oil preferably comprises a polyoxyethylene castor oil selected from the group consisting of polyoxyl 5 castor oil, polyoxyl 9 castor oil, polyoxyl 15 castor oil, polyoxyl 35 castor oil, and polyoxyl 40 castor oil.

10 Claims, No Drawings

(56) References Cited

U.S. PATENT DOCUMENTS

| | | | |
|---|---|---|---|
| 2018/0169079 A1 | 6/2018 | Shams et al. |
| 2019/0060459 A1 | 2/2019 | Endo |
| 2019/0105310 A1 | 4/2019 | Shams et al. |
| 2020/0046839 A1 | 2/2020 | Endo |
| 2020/0113880 A1 | 4/2020 | Endo |

FOREIGN PATENT DOCUMENTS

| | | | |
|---|---|---|---|
| CN | 102448940 | A | 5/2012 |
| EP | 2415763 | A1 | 2/2012 |
| EP | 3093018 | A1 | 11/2016 |
| EP | 3093019 | A1 | 11/2016 |
| EP | 3093021 | A1 | 11/2016 |
| JP | H11500122 | A | 1/1999 |
| JP | 2002509101 | A | 3/2002 |
| JP | 2002356420 | A | 12/2002 |
| JP | 3631255 | B2 | 3/2005 |
| JP | 2009114183 | A | 5/2009 |
| JP | 2010100652 | A | 5/2010 |
| JP | 2011057633 | A | 3/2011 |
| JP | 2012180346 | A | 9/2012 |
| JP | 2013151548 | A | 8/2013 |
| JP | 2014019650 | A | 2/2014 |
| JP | 6012775 | B2 | 10/2016 |
| KR | 1020120003475 | | 1/2012 |
| TW | 201340960 | A | 10/2013 |
| WO | 9729752 | A1 | 8/1997 |
| WO | 2009113600 | A1 | 9/2009 |
| WO | 2010113957 | A1 | 10/2010 |
| WO | 2012141334 | A1 | 10/2012 |
| WO | 2013146649 | A1 | 10/2013 |
| WO | 2014010354 | A1 | 1/2014 |
| WO | 2014010654 | A2 | 1/2014 |
| WO | 2015105134 | A1 | 7/2015 |
| WO | 2015105135 | A1 | 7/2015 |
| WO | 2015105144 | A1 | 7/2015 |

OTHER PUBLICATIONS

EPO Extended European Search Report corresponding to EP Application No. 15735316.0-1468/3093019 PCT/JP2015050334; Mailing date of Jun. 23, 2017.

EPO Extended European Search Report for corresponding EP Application No. 15735607.2-1468/3093021 PCT/JP2015050333; Mailing date of Jun. 23, 2017.

Fouquet el al., Journal of Oleo Science, ISSN 1347-3352 online, Aug. 8, 2017, pp. 1-12.

IN Office Action for corresponding IN Application No. 201617026272; Dated Jun. 19, 2019.

International Search Report for corresponding International Application No. PCT/JP2015/050333; Date of Mailing: Mar. 31, 2015.

International Search Report for corresponding International Application No. PCT/JP2015/050334; Date of Mailing: Mar. 31, 2015.

IP Office of Singapore Written Opinion for corresponding SG Application No. 11201605366Q; Mailing date of May 15, 2017.

KIPO Office Action for corresponding KR Application No. 10-2016-7016405; Dated Nov. 27, 2020.

JPO Notification of Reasons for Refusal for corresponding JP Application No. 2015-002272, mailed Aug. 14, 2018.

JPO Notification of Reasons for Refusal for corresponding JP Application No. 2016-181739; Mailing date of Aug. 28, 2018.

NZIPO Office Action for corresonding NZ Application No. 722144; dated, Mar. 12, 2021.

NZIPO Office Action for corresponding NZ Application No. 721530; Dated Dec. 17, 2020.

Polyoxyl Castor Oil Polyoxyl Hydrogenated Castor Oil, Summary Report, The European Agency for the Evaluation of Medicinal Products, EMEA/MRL/614/99-FINAL, Jun. 1999, available at https://www.ema.europa.eu/en/documents/mri-report/polyoxyl-castor-oil-polyoxyl-hydrogenated-castor-oil-summary-report-committee-veterina.

SIPO Office Action corresponding to Application No. 201580003108.9; Mailing date of Aug. 4, 2017.

IPOPH Substantive Examination Report issued to PH Patent Application No. 1-2016-501328, mailed Aug. 17, 2018.

TIPO Office Action corresponding to TW Application No. 104100528; Mailing date of Jun. 19, 2018.

Tubez et al., "Manual of usual raw materials for fine chemical formulations", Eds., Guangdong Sci. Press, p. 1111, Pub. 19980331*see English Translation of CN Office Action for concise explanation of relevance.

USPTO Non-Final Office Action for corresponding U.S. Appl. No. 15/204,507; Dated Oct. 3, 2017.

USPTO Non-Final Office Action for corresponding U.S. Appl. No. 16/658,585; notification date Feb. 5, 2020.

USPTO Final Office Action for corresponding U.S. Appl. No. 15/204,475; Dated Apr. 11, 2018.

USPTO Final Office Action for corresponding U.S. Appl. No. 15/204,507; Dated Mar. 16, 2018.

USPTO Final Office Action for corresponding U.S. Appl. No. 16/711,706, Issued on Mar. 18, 2021.

USPTO Non-Final Office Action for corresponding U.S. Appl. No. 15/204,475; Dated Apr. 30, 2020.

USPTO Non-Final Office Action for corresponding U.S. Appl. No. 15/204,475; Dated Nov. 2, 2018.

USPTO Non-Final Office Action for corresponding U.S. Appl. No. 15/204,475; Dated Sep. 22, 2017.

USPTO Non-Final Office Action for corresponding U.S. Appl. No. 16/942,877, Issued on Jan. 31, 2023.

USPTO Non-Final Office for corresponding U.S. Appl. No. 16/173,299; Mailing date of Mar. 28, 2019.

* cited by examiner

PYRIDYLAMINOACETIC ACID COMPOUND AND POLYOXYETHYLENE CASTOR OIL-CONTAINING PHARMACEUTICAL COMPOSITION

CROSS REFERENCE TO RELATED APPLICATIONS

This application is a continuation of U.S. patent application Ser. No. 16/711,706 filed on Dec. 12, 2019, which is a continuation of Ser. No. 15/204,475, filed on Jul. 7, 2016, now abandoned. Ser. No. 15/204,475 is a continuation of PCT/JP2015/050333 filed on Jan. 8, 2015, and which claims priority to Japanese Application No. 2014-002809, filed Jan. 10, 2014, the entire contents of which in their entirety are incorporated herein by reference.

TECHNICAL FIELD

The present invention relates to a pharmaceutical composition comprising Isopropyl(6-{[4-(pyrazol-1-yl)benzyl](pyridin-3-ylsulfonyl)aminomethyl}pyridin-2-ylamino)acetate or a salt thereof, and a method for stabilizing the compound or salt thereof.

BACKGROUND ART

Isopropyl(6-{[4-(pyrazol-1-yl)benzyl](pyridin-3ylsulfonyl)aminomethyl}pyridin-2-ylamino)acetate is a compound represented by the following formula (1):

(1)

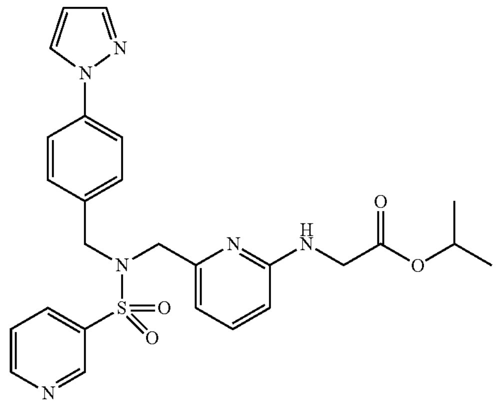

Patent Document 1 and Patent Document 2 mention pyridylaminoacetic acid compounds such as isopropyl (6-{[4-(pyrazol-1-yl)benzyl](pyridin-3-ylsulfonyl)aminomethyl}pyridin-2-ylamino)acetate, and Patent Document 1 mentions, as eye drops of the pyridylaminoacetic acid compound, Formulation Examples comprising concentrated glycerol and Polysorbate 80.

However, Patent Document 1 does not mention a pharmaceutical composition comprising isopropyl (6-{[4-(pyrazol-1-yl)benzyl](pyridin-3-ylsulfonyl)aminomethyl}pyridin-2-ylamino)acetate or a salt thereof and polyoxyethylene castor oil, and also there is absolutely no mention that polyoxyethylene castor oil improves stability of the isopropyl (6-{[4-(pyrazol-1-yl)benzyl](pyridin-3-ylsulfonyl)aminomethyl}pyridin-2-ylamino)acetate or salt thereof in the pharmaceutical composition.

Patent Document 1: U.S. Published Patent Application Publication, No. 2012/0190852, Specification Patent Document 2: U.S. Published Patent Application Publication, No. 2011/0054172, Specification

DISCLOSURE OF THE INVENTION

Problems to be Solved by the Invention

At a stage of development of a pharmaceutical composition comprising isopropyl (6-{[4-(pyrazol-1-yl)benzyl](pyridin-3-ylsulfonyl)aminomethyl}pyridin-2-ylamino)acetate or a salt thereof (hereinafter also referred to as "the present compound"), the present inventors have found that, in an aqueous composition comprising the present compound dissolved therein, stability of the present compound is inferior.

An object of the present invention is to provide a pharmaceutical composition comprising the present compound, in which the present compound in the pharmaceutical composition is stable. Another object of the present invention is to provide a method for improving stability of the present compound in the pharmaceutical composition.

Means for Solving the Problems

The present inventors have intensively studied about a surfactant for dissolving the present compound so as to achieve the above objects, and found that the present compound in a pharmaceutical composition has a high remaining rate even under long-term storage when using polyoxyethylene castor oil, thus completing the present invention. Namely, the present invention is related to the following.

(1) A pharmaceutical composition comprising isopropyl (6-{[4-(pyrazol-1-yl)benzyl](pyridin-3-ylsulfonyl)aminomethyl}pyridin-2-ylamino)acetate or a salt thereof, and polyoxyethylene castor oil.

(2) The pharmaceutical composition according to (1), wherein the polyoxyethylene castor oil includes polyoxyethylene castor oil selected from the group consisting of polyoxyl 5 castor oil, polyoxyl 9 castor oil, polyoxyl 15 castor oil, polyoxyl 35 castor oil, and polyoxyl 40 castor oil.

(3) The pharmaceutical composition according to (2), wherein the polyoxyethylene castor oil include polyoxyl 35 castor oil.

(4) The pharmaceutical composition according to any one of (1) to (3), wherein the content of 6-{[4-(pyrazol-1-yl)benzyl](pyridin-3-ylsulfonyl)aminomethyl}pyridin-2-ylamino)isopropyl acetate or a salt thereof is in a range of 0.0001 to 0.1% (w/v).

(5) The pharmaceutical composition according to (4), wherein the content of 6-{[4-(pyrazol-1-yl)benzyl](pyridin-3-ylsulfonyl)aminomethyl}pyridin-2-ylamino)isopropyl acetate or a salt thereof is in a range of 0.001 to 0.003% (w/v).

(6) The pharmaceutical composition according to any one of (1) to (5), wherein the content of the polyoxyethylene castor oil is in a range of 0.001 to 5% (w/v).

(7) The pharmaceutical composition according to (6), wherein the content of the polyoxyethylene castor oil is in a range of 0.8 to 2% (w/v).

(8) The pharmaceutical composition according to any one of (1) to (7), wherein the content of the polyoxyethylene castor oil is in a range of 1 to 20,000 parts by mass relative to 1 part by mass of 6-{[4-(pyrazol-1-yl)benzyl](pyridin-3-ylsulfonyl)aminomethyl}pyridin-2-ylamino)isopropyl acetate or a salt thereof.

(9) The pharmaceutical composition according to (8), wherein the content of the polyoxyethylene castor oil is in a range of 200 to 2,000 parts by mass relative to 1 part by mass of 6-{[4-(pyrazol-1-yl)benzyl](pyridin-3-ylsulfonyl)aminomethyl}pyridin-2-ylamino)isopropyl acetate or a salt thereof.

(10) The pharmaceutical composition according to any one of (1) to (9), which further comprises edetic acid or a salt thereof.

(11) The pharmaceutical composition according to any one of (1) to (10), which further comprises boric acid or a salt thereof, citric acid or a salt thereof, or acetic acid or a salt thereof

(12) The pharmaceutical composition according to any one of (1) to (11), which does not comprise sorbic acid.

(13) The pharmaceutical composition according to any one of (1) to (12), which is filled into a container made of polyethylene.

(14) The pharmaceutical composition according to any one of (1) to (13), for prevention or treatment of glaucoma or ocular hypertension, or for reduction of intraocular pressure.

(15) A method for stabilizing isopropyl (6-{[4-(pyrazol-1-yl)benzyl](pyridin-3-ylsulfonyl) aminomethyl}pyridin-2-ylamino)acetate or a salt thereof by allowing a pharmaceutical composition comprising isopropyl (6-{[4-(pyrazol-1-yl)benzyl] (pyridin-3-ylsulfonyl)aminomethyl}pyridin-2-ylamino)acetate or a salt thereof to comprise polyoxyethylene castor oil.

The respective structures of the above-mentioned (1) to (15) can be combined by optionally selecting two or more structures therefrom.

Effects of the Invention

According to the present invention, it is possible to provide a pharmaceutical composition in which the present compound in the pharmaceutical composition is stabilized over a long period of time. The pharmaceutical composition of the present invention has enough safety as a pharmaceutical product. According to the present invention, it is also possible to provide a method for stabilizing the present compound in a pharmaceutical composition over a long period of time. According to the present invention, it is also possible to provide a method for using polyoxyethylene castor oil so as to produce a pharmaceutical composition in which the present compound in the pharmaceutical composition is stabilized over a long period of time.

PREFERRED MODE FOR CARRYING OUT THE INVENTION

Embodiments of the present invention will be described in detail below.

It is possible to produce isopropyl (6-{[4-(pyrazol-1-yl) benzyl](pyridin-3-ylsulfonyl)aminomethyl}pyridin-2-ylamino)acetate or a salt thereof comprised in a pharmaceutical composition of the present invention in accordance with a conventional method in the technical field, such as a method mentioned in U.S. Published Patent Application Publication, No. 2012/0190852, Specification.

In the pharmaceutical composition of the present invention, a salt of isopropyl (6-{[4-(pyrazol-1-yl)benzyl](pyridin-3-ylsulfonyl)aminomethyl}pyridin-2-ylamino)acetate is not particularly limited as long as it is a pharmacologically acceptable salt. Specifically, there are exemplified inorganic acid salts such as hydrochlorides, hydrobromates, hydroiodides, nitrates, sulfates, or phosphates; or organic acid salts such as acetates, trifluoroacetates, benzoates, oxalates, malonates, succinates, maleates, fumarates, tartrates, citrates, methanesulfonates, ethanesulfonates, trifluoromethanesulfonates, benzenesulfonates, p-toluenesulfonates, glutamates, or aspartates. Preferably, hydrochlorides or trifluoroacetates are exemplified.

In the pharmaceutical composition of the present invention, the content of isopropyl(6-{[4-(pyrazol-1-yl)benzyl] (pyridin-3-ylsulfonyl)aminomethyl}pyridin-2-ylamino)acetate or a salt thereof is not particularly limited. Specifically, the lower limit is preferably 0.0001% (w/v), more preferably 0.0003% (w/v), still more preferably 0.0005% (w/v), and yet still more preferably 0.001% (w/v). The upper limit is preferably 0.1% (w/v), more preferably 0.03% (w/v), still more preferably 0.01% (w/v), yet still more preferably 0.008% (w/v), even still more preferably 0.005% (w/v), and particularly preferably 0.003% (w/v). More specifically, the content is preferably in a range of 0.0001 to 0.1% (w/v), more preferably 0.0003 to 0.03% (w/v), still more preferably 0.0005 to 0.01% (w/v), yet still more preferably 0.001 to 0.008% (w/v), even still more preferably 0.001 to 0.005% (w/v), and particularly preferably 0.001 to 0.003% (w/v). Comparatively small content of the present compound may enable a reduction in amount of a surfactant (typically polyoxyethylene castor oil), which is required to dissolve the present compound, so that the content of the present compound is preferably less than 0.01% (w/v). When comprising a salt of isopropyl (6-{[4-(pyrazol-1-yl)benzyl](pyridin-3-ylsulfonyl)aminomethyl}pyridin-2-ylamino)acetate, it means that the content of isopropyl (6-{[4-(pyrazol-1-yl) benzyl](pyridin-3-ylsulfonyl)aminomethyl}pyridin-2-ylamino)acetate falls in the above range in a state where the salt is isolated.

In the pharmaceutical composition of the present invention, it is possible to use, as the polyoxyethylene castor oil, various polyoxyethylene castor oils each exhibiting different number of polymerization of ethylene oxide. The number of polymerization of ethylene oxide is preferably in a range of 5 to 100, more preferably 20 to 50, particularly preferably 30 to 40, and most preferably 35. Specific examples of the polyoxyethylene castor oil include polyoxyl 5 castor oil, polyoxyl 9 castor oil, polyoxyl 15 castor oil, polyoxyl 35 castor oil, polyoxyl 40 castor oil, and the like, and polyoxyl 35 castor oil is most preferable. The polyoxyethylene castor oil as used herein is not polyoxyethylene hardened castor oil (provided that it is not excluded from the present invention that the pharmaceutical composition of the present invention further comprises polyoxyethylene hardened castor oil in the amount which does not exert an adverse influence on stability).

In the pharmaceutical composition of the present invention, the content of the polyoxyethylene castor oil is not particularly limited. Specifically, the lower limit is preferably 0.001% (w/v), more preferably 0.01% (w/v), still more preferably 0.1% (w/v), particularly preferably 0.5% (w/v), and most preferably 0.8% (w/v). The upper limit is preferably 10% (w/v), more preferably 5% (w/v), still more preferably 4% (w/v), particularly preferably 3% (w/v), and most preferably 2% (w/v). More specifically, the content is preferably in a range of 0.001 to 10% (w/v), more preferably 0.01 to 5% (w/v), still more preferably 0.1 to 4% (w/v), particularly preferably 0.5 to 3% (w/v), and most preferably 0.8 to 2% (w/v).

In the pharmaceutical composition of the present invention, the content of the polyoxyethylene castor oil relative to 6-{[4-(pyrazol-1-yl)benzyl](pyridin-3-ylsulfonyl) aminomethyl}pyridin-2-ylamino)isopropyl acetate or a salt thereof is not particularly limited. Specifically, the lower limit of the content of the polyoxyethylene castor oil is preferably 1 part by mass, more preferably 10 parts by mass, still more preferably 50 parts by mass, yet still more preferably 100 parts by mass, and particularly preferably 200 parts by mass, relative to 1 part by mass of 6-{[4-(pyrazol-1-yl)benzyl](pyridin-3-ylsulfonyl) aminomethyl}pyridin-2-ylamino)isopropyl acetate or a salt thereof. The upper limit is preferably 20,000 parts by mass, more preferably 10,000 parts by mass, still more preferably 5,000 parts by mass, yet still more preferably 3,000 parts by mass, and particularly preferably 2,000 parts by mass. More specifically, the content of the polyoxyethylene castor oil is preferably in a range of 1 to 20,000 parts by mass, more preferably 10 to 10,000 parts by mass, still more preferably 50 to 5,000 parts by mass, particularly preferably 100 to 3,000 parts by mass, and most preferably 200 to 2,000 parts by mass, relative to 1 part by mass of 6-{[4-(pyrazol-1-yl) benzyl](pyridin-3-ylsulfonyl)aminomethyl}pyridin-2-ylamino)isopropyl acetate or a salt thereof.

Additives can be optionally used in the pharmaceutical composition of the present invention, and it is possible to add, as additives, a buffer agent, a tonicity agent, a stabilizer, a preservative, an antioxidant, a high molecular weight polymer, and the like.

It is possible to mix the buffer agent, which is usable as additives for a pharmaceutical product, in the pharmaceutical composition of the present invention. Examples of the buffer agent include phosphoric acid or a salt thereof, boric acid or a salt thereof, citric acid or a salt thereof, acetic acid or a salt thereof, carbonic acid or a salt thereof, tartaric acid or a salt thereof, ε-aminocaproic acid, trometamol, and the like. From a viewpoint of buffering capacity in a weak acid region, the buffer agent is preferably boric acid or a salt thereof, citric acid or a salt thereof, or acetic acid or a salt thereof, and particularly preferably citric acid or a salt thereof. Examples of the phosphate include sodium phosphate, sodium dihydrogen phosphate, disodium hydrogen phosphate, potassium phosphate, potassium dihydrogen phosphate, dipotassium hydrogen phosphate, and the like; examples of the borate include borax, sodium borate, potassium borate, and the like; examples of the citrate include sodium acetate, disodium citrate, trisodium citrate, and the like; examples of the acetate include sodium acetate, potassium acetate, and the like; examples of the carbonate include sodium carbonate, sodium hydrogen carbonate, and the like; and examples of the tartrate include sodium tartrate, potassium tartrate, and the like. When the buffer agent is mixed in the pharmaceutical composition of the present invention, the content of the buffer agent can be appropriately adjusted according to the type of the buffer agent, and is preferably in a range of 0.001 to 10% (w/v), more preferably 0.01 to 5% (w/v), still more preferably 0.1 to 3% (w/v), and most preferably 0.2 to 2% (w/v).

It is possible to appropriately mix the tonicity agent, which is usable as additives for a pharmaceutical product, in the pharmaceutical composition of the present invention. Examples of the tonicity agent include an ionic tonicity agent, a nonionic tonicity agent, and the like. Examples of the ionic tonicity agent include sodium chloride, potassium chloride, calcium chloride, magnesium chloride, and the like; and examples of the nonionic tonicity agent include glycerol, propylene glycol, sorbitol, mannitol, and the like. When the tonicity agent is mixed in the pharmaceutical composition of the present invention, the content of the tonicity agent can be appropriately adjusted according to the type of the tonicity agent, and is preferably in a range of 0.01 to 10% (w/v), more preferably 0.02 to 7% (w/v), still more preferably 0.1 to 5% (w/v), particularly preferably 0.5 to 4% (w/v), and most preferably 0.8 to 3% (w/v).

It is possible to appropriately mix the stabilizer, which is usable as additives for a pharmaceutical product, in the pharmaceutical composition of the present invention. Examples of the stabilizer include edetic acid, monosodium edetate, disodium edetate, tetrasodium edetate, sodium citrate, and the like, and disodium edetate is particularly preferable. When the stabilizer is mixed in the pharmaceutical composition of the present invention, the content of the stabilizer can be appropriately adjusted according to the type of the stabilizer, and is preferably in a range of 0.001 to 1% (w/v), more preferably 0.005 to 0.5% (w/v), still more preferably 0.01 to 0.1% (w/v), and most preferably 0.02 to 0.05% (w/v).

It is possible to appropriately mix the preservative, which is usable as additives for a pharmaceutical product, in the pharmaceutical composition of the present invention. Examples of the preservative include benzalkonium chloride, benzalkonium bromide, benzethonium chloride, sorbic acid, potassium sorbate, methyl paraoxybenzoate, propyl paraoxybenzoate, chlorobutanol, and the like. From a viewpoint of stability of 6-{[4-(pyrazol-1-yl)benzyl](pyridin-3-ylsulfonyl)aminomethyl}pyridin-2-ylamino)isopropyl acetate or a salt thereof, it is desired not to include sorbic acid. When the preservative is mixed in the pharmaceutical composition of the present invention, the content of the preservative can be appropriately adjusted according to the type of the preservative, and is preferably in a range of 0.0001 to 1% (w/v), more preferably 0.0005 to 0.1% (w/v), still more preferably 0.001 to 0.05% (w/v), and most preferably 0.002 to 0.01% (w/v).

It is possible to appropriately mix the antioxidant, which is usable as additives for a pharmaceutical product, in the pharmaceutical composition of the present invention. Examples of the antioxidant include ascorbic acid, tocopherol, dibutylhydroxytoluene, butylhydroxyanisole, sodium erythorbate, propyl gallate, sodium sulfite, and the like. When the antioxidant is mixed in the pharmaceutical composition of the present invention, the content of the antioxidant can be appropriately adjusted according to the type of the antioxidant, and is preferably in a range of 0.0001 to 1% (w/v), more preferably 0.0005 to 0.1% (w/v), still more preferably 0.001 to 0.02% (w/v), and most preferably 0.005 to 0.010% (w/v).

It is possible to appropriately mix the high molecular weight polymer, which is usable as additives for a pharmaceutical product, in the pharmaceutical composition of the present invention. Examples of the high molecular weight polymer include methyl cellulose, ethyl cellulose, hydroxymethyl cellulose, hydroxyethyl cellulose, hydroxypropyl cellulose, hydroxyethylmethyl cellulose, hydroxypropylmethyl cellulose, carboxymethyl cellulose, sodium carboxymethyl cellulose, hydroxypropylmethylcellulose acetate succinate, hydroxypropylmethylcellulose phthalate, carboxymethylethyl cellulose, cellulose acetate phthalate, polyvinylpyrrolidone, polyvinyl alcohol, carboxyvinyl polymer, polyethylene glycol, and the like. When the high molecular weight polymer is mixed in the pharmaceutical composition of the present invention, the content of the high molecular weight polymer can be appropriately adjusted according to the type of the high molecular weight polymer, and is preferably in a range of 0.001 to 5% (w/v), more preferably 0.01 to 1% (w/v), and still more preferably 0.1 to 0.5% (w/v).

The pH of the pharmaceutical composition of the present invention is preferably in a range of 4.0 to 8.0, more preferably 4.5 to 7.5, and most preferably 5.0 to 7.0.

The pharmaceutical composition of the present invention can be stored in a container made of various raw materials. For example, it is possible to use containers made of polyethylene, polypropylene, and the like. From a viewpoint of ease of instillation (hardness of container) and stability of the present compound, it is preferred to store in a container made of polyethylene.

The dosage form of the pharmaceutical composition of the present invention is not particularly limited as long as it is usable as a pharmaceutical product. Examples of the dosage form include eye drop, ophthalmic injection, and the like, and eye drop is particularly preferable. They can be produced in accordance with a conventional method in the technical field. The pharmaceutical composition of the present invention is basically a solution, and a solvent or dispersion medium thereof is preferably water.

The pharmaceutical composition of the present invention is useful for prevention or treatment of glaucoma or ocular hypertension, or for reduction of intraocular pressure. Examples of glaucoma in the present invention include primary open-angle glaucoma, secondary open-angle glaucoma, normal tension glaucoma, hypersecretion glaucoma, primary closed-angle glaucoma, secondary closed-angle glaucoma, plateau iris glaucoma, mixed glaucoma, developmental glaucoma, steroid glaucoma, exfoliation glaucoma, amyloid glaucoma, neovascular glaucoma, malignant glaucoma, capsular glaucoma, plateau iris syndrome, and the like.

The pharmaceutical composition of the present invention may comprise one or plurality of, preferably 1 to 3 of, and more preferably one or two other glaucoma or ocular hypertension therapeutic agent(s) or intraocular tension depressor(s). The other glaucoma therapeutic agents is not particularly limited. Specifically, the other glaucoma therapeutic agent is preferably a commercially available glaucoma therapeutic agent or a glaucoma therapeutic agent under development, more preferably a commercially available glaucoma therapeutic agent, and particularly preferably a commercially available glaucoma therapeutic agent whose mechanism of action is different from that of the present compound. More specifically, there are exemplified a non-selective sympathomimetic agent, an α2 receptor agonist, an al receptor antagonist, a R receptor antagonist, a parasympatholytic agent, a carbonate dehydratase inhibitor, prostaglandins, a Rho kinase inhibitor, and the like. Specific examples of the non-selective sympathomimetic agent include dipivefrin; specific examples of the α2 receptor agonist include brimonidine and apraclonidine; specific examples of the al receptor antagonist include bunazosin; specific examples of the β receptor antagonist include timolol, befunolol, carteolol, nipradilol, betaxolol, levobunolol, and metipranolol; specific examples of the parasympatholytic agent include pilocarpine; specific examples of the carbonate dehydratase inhibitor include dorzolamide, brinzolamide, and acetazolamide; specific examples of prostaglandins include latanoprost, isopropyl unoprostone, bimatoprost, and travoprost; and specific examples of the Rho kinase inhibitor include ripasudil.

EXAMPLES

Formulation Examples and test results will be shown below, but such are for better understanding of the present invention and do not limit the scope of the present invention.

FORMULATION EXAMPLES

Typical Formulation Examples using the present compound will be shown below. In the following Formulation Examples, the mixing amount of each component is the content in 100 mL of the composition.

Formulation Example 1

Eye drop (in 100 mL)
Present compound 0.001 g
Boric acid 0.2 g
Glycerol 2.0 g
Polyoxyl 35 castor oil 0.5 g
Disodium edetate 0.05 g
Benzalkonium chloride 0.005 g
Dilute hydrochloric acid q.s.
Sodium hydroxide q.s.
Purified water q.s.

Formulation Example 2

Eye drop (in 100 mL)
Present compound 0.001 g
Sodium dihydrogen phosphate 0.2 g
Glycerol 2.0 g
Polyoxyl 35 castor oil 0.8 g
Disodium edetate 0.05 g
Benzalkonium chloride 0.005 g
Dilute hydrochloric acid q.s.
Sodium hydroxide q.s.
Purified water q.s.

Formulation Example 3

Eye drop (in 100 mL)
Present compound 0.001 g
Trisodium citrate 0.2 g
Glycerol 2.0 g
Polyoxyl 35 castor oil 0.3 g
Disodium edetate 0.05 g
Benzalkonium chloride 0.005 g
Dilute hydrochloric acid q.s.
Sodium hydroxide q.s.
Purified water q.s.

Types and mixing amounts of the present compound, polyoxyethylene castor oil, and additives in Formulation Examples 1 to 3 can be appropriately adjusted to obtain desired compositions.

1. Stability Evaluation Test (1)

An influence of a surfactant on stability of the present compound was studied.

1-1. Preparation of Test Formulation

To 5 g of polyoxyl 35 castor oil, 20 mL of a 10% sodium dihydrogen phosphate solution and 900 mL of purified water were added. After adjusting the pH to about 6 by adding a sodium hydroxide solution or dilute hydrochloric acid (q.s.), 0.003 g of isopropyl (6-{[4-(pyrazol-1-yl)benzyl](pyridin-3-ylsulfonyl)aminomethyl}pyridin-2-ylamino)acetate (hereinafter also referred to as the compound A) was added and dissolved. To this was added purified water (q.s.) to make 1,000 mL in total, thus preparing a formulation of Example 1.

In the same manner as in preparation method of Example 1, formulations of Comparative Examples 1 and 2 shown in Table 1 were prepared.

1-2. Test Procedure

After filling a glass ampule with 5 mL of a test formulation and storing at 60° C. for an optional period, the content of isopropyl (6-{[4-(pyrazol-1-yl)benzyl](pyridin-3-ylsulfonyl)aminomethyl}pyridin-2-ylamino)acetate was determined using high-performance liquid chromatography, and then a remaining rate (%) thereof was calculated.

1-3. Test Results and Consideration

Test results are shown in Table 1.

TABLE 1

| % (w/v) | | Example 1 | Comparative Example 1 | Comparative Example 2 |
|---|---|---|---|---|
| Present compound A | | 0.0003 | 0.0003 | 0.0003 |
| Polyoxyl 35 castor oil | | 0.5 | — | — |
| Polyoxyethylene hardened castor oil 60 | | — | 0.5 | — |
| Polysorbate 80 | | — | — | 0.5 |
| Sodium dihydrogen phosphate | | 0.2 | 0.2 | 0.2 |
| HCl/NaOH | | q.s. | q.s. | q.s. |
| Purified water | | q.s. | q.s. | q.s. |
| pH | | 6 | 6 | 6 |
| Remaining rate (%) | 60° C./ 1 week | 96.4 | 24.2 | 69.5 |
| | 60° C./ 4 weeks | 71.7 | ND | ND |

ND: no data

As is apparent from Table 1, the formulation of Example 1 maintained significantly high remaining rate at 60° C. over 4 weeks, as compared with the formulations of Comparative Examples 1 and 2. The results revealed that the pharmaceutical composition of the present invention has excellent stability.

2. Stability Evaluation Test (2)

An influence of additives and pH in the pharmaceutical composition of the present invention was studied.

2-1. Preparation of Test Formulation

In the same manner as in preparation method of Example 1, the formulations of Examples 2 to 24 shown in Tables 2 to 6 were prepared.

2-2. Test Procedure

After filling a glass ampule with 5 mL of a test formulation and storing at 60° C. for an optional period, the content of isopropyl (6-{[4-(pyrazol-1-yl)benzyl](pyridin-3-ylsulfonyl)aminomethyl}pyridin-2-ylamino)acetate was determined using high-performance liquid chromatography, and then a remaining rate (%) thereof was calculated.

TABLE 2

| % (w/v) | | Example 2 | Example 3 | Example 4 | Example 5 | Example 6 | Example 7 |
|---|---|---|---|---|---|---|---|
| Present compound A | | 0.01 | 0.01 | 0.0003 | 0.001 | 0.01 | 0.03 |
| Polyoxyl 35 castor oil | | 0.8 | 0.8 | 0.5 | 0.8 | 2 | 2 |
| Sodium dihydrogen phosphate | | 0.2 | 0.2 | 0.2 | 0.2 | 0.2 | 0.2 |
| Sodium edetate hydrate | | 0.01 | — | 0.05 | 0.05 | 0.05 | 0.05 |
| Glycerol | | 2.3 | 2.3 | — | 2.3 | 2.3 | 2.3 |
| Benzalkonium chloride | | 0.004 | 0.004 | — | 0.004 | 0.004 | 0.00 |
| HCl/NaOH | | q.s. | q.s. | q.s. | q.s. | q.s. | q.s. |
| Purified water | | q.s. | q.s. | q.s. | q.s. | q.s. | q.s. |
| PH | | 5.8 | 5.8 | 6.0 | 5.8 | 5.8 | 5.8 |
| Remaining rate (%) | 60° C./ 2 weeks | 94.5 | 88.6 | ND | 93.2 | 94.0 | 94.1 |
| | 60° C./ 4 weeks | 86.2 | 73.0 | 83.2 | 82.2 | 87.1 | 90.9 |

ND: no data

TABLE 3

| % (w/v) | Example 8 | Example 9 | Example 10 | Example 11 | Example 12 | Example 13 | Example 14 |
|---|---|---|---|---|---|---|---|
| Present compound A | 0.003 | 0.003 | 0.003 | 0.003 | 0.003 | 0.01 | 0.01 |
| Polyoxyl 35 castor oil | 0.8 | 0.8 | 0.8 | 0.8 | 0.8 | 0.8 | 0.8 |
| Sodium dihydrogen phosphate | 0.2 | — | — | — | — | — | — |
| Boric acid | — | 1 | — | — | — | 1 | — |

TABLE 3-continued

| % (w/v) | | Example 8 | Example 9 | Example 10 | Example 11 | Example 12 | Example 13 | Example 14 |
|---|---|---|---|---|---|---|---|---|
| Trisodium citratedihydrate | | — | — | 0.2 | — | — | — | — |
| Sodium acetatetrihydrate | | — | — | — | 0.2 | — | — | — |
| ε-Aminocaproic acid | | — | — | — | — | 0.2 | — | — |
| Trometamol | | — | — | — | — | — | — | 0.9 |
| Sodium edetate hydrate | | 0.02 | 0.02 | 0.02 | 0.02 | 0.02 | 0.05 | 0.05 |
| Glycerol | | 2.2 | 1.0 | 2.2 | 2.2 | 2.2 | 1.4 | 0.8 |
| Benzalkonium chloride | | 0.004 | 0.004 | 0.004 | 0.004 | 0.004 | 0.004 | 0.004 |
| HCl/ NaOH | | q.s. | q.s. | q.s. | q.s. | q.s. | q.s. | q.s. |
| Purified water | | q.s. | q.s. | q.s. | q.s. | q.s. | q.s. | q.s. |
| pH | | 6.0 | 6.0 | 6.0 | 6.0 | 6.0 | 5.8 | 5.8 |
| Remaining rate (%) | 60° C./ 2 weeks | 94.6 | 94.0 | 95.1 | 94.3 | 94.4 | 93.1 | 92.6 |

TABLE 4

| % (w/v) | | Example 15 | Example 16 | Example 17 | Example 18 |
|---|---|---|---|---|---|
| Present compound A | | 0.01 | 0.01 | 0.01 | 0.01 |
| Polyoxyl 35 castor oil | | 0.8 | 0.8 | 0.8 | 0.8 |
| Sodium dihydrogen phosphate | | 0.2 | 0.2 | 0.2 | 0.2 |
| Sodium edetate hydrate | | 0.05 | 0.05 | 0.05 | 0.05 |
| Glycerol | | 2.3 | 2.3 | 2.3 | 2.3 |
| Benzalkonium chloride | | 0.002 | 0.008 | 0.004 | 0.004 |
| HCl/NaOH | | q.s. | q.s. | q.s. | q.s. |
| Purified water | | q.s. | q.s. | q.s. | q.s. |
| pH | | 5.8 | 5.8 | 5.0 | 6.5 |
| Remaining rate (%) | 60° C./ 2 weeks | 95.3 | 94.1 | 94.8 | 92.6 |

TABLE 5

| % (w/v) | | Example 19 | Example 20 | Example 21 | Example 22 |
|---|---|---|---|---|---|
| Present compound A | | 0.003 | 0.003 | 0.003 | 0.003 |
| Polyoxyl 35 castor oil | | 0.8 | 0.8 | 0.8 | 0.8 |
| Boric acid | | 1 | 1 | — | — |
| ε-Aminocaproic acid | | — | — | 0.2 | 0.2 |
| Sodium edetate hydrate | | 0.02 | 0.02 | 0.02 | 0.02 |
| Glycerol | | 1 | — | 2.3 | — |
| Mannitol | | — | 2 | — | 4.5 |
| Benzalkonium chloride | | 0.0013 | 0.0013 | 0.0013 | 0.0013 |
| HCl/NaOH | | q.s. | q.s. | q.s. | q.s. |
| Purified water | | q.s. | q.s. | q.s. | q.s. |
| pH | | 6.0 | 6.0 | 6.0 | 6.0 |
| Remaining rate (%) | 60° C./ 2 weeks | 93.3 | 93.0 | 93.4 | 93.6 |

TABLE 6

| % (w/v) | | Example 23 | Example 24 |
|---|---|---|---|
| Present compound A | | 0.0003 | 0.0003 |
| Polyoxyl 35 castor oil | | 0.8 | 0.8 |
| Boric acid | | 1 | 1 |

TABLE 6-continued

| % (w/v) | | Example 23 | Example 24 |
|---|---|---|---|
| Sorbic acid | | 0.1 | — |
| Sodium edetate hydrate | | 0.05 | 0.05 |
| Glycerol | | 1 | 1 |
| Benzalkonium chloride | | 0.01 | 0.01 |
| HCl/NaOH | | q.s. | q.s. |
| Purified water | | q.s. | q.s. |
| PH | | 6.5 | 6.5 |
| Remaining rate (%) | 60° C. 2 weeks | 89.1 | 92.5 |

As is apparent from Tables 2 to 6, the formulations of Examples 2 to 24 maintained a high remaining rate at 60° C. over 2 or 4 weeks.

The invention claimed is:

1. A method for stabilizing isopropyl (6-{[4-(pyrazol-1-yl)benzyl](pyridin-3-ylsulfonyl)aminomethyl}pyridin-2-ylamino)acetate or a salt thereof, the method comprising preparing a pharmaceutical composition by combining (i) isopropyl (6-{[4-(pyrazol-1-yl)benzyl](pyridin-3-ylsulfo-nyl)aminomethyl}pyridin-2-ylamino)acetate or a salt thereof as a sole active ingredient, (ii) citric acid or a salt thereof, (iii) polyoxyethylene castor oil, and (iv) glycerin, wherein the content of the isopropyl (6-{[4-(pyrazol-1-yl)benzyl] (pyridin-3-ylsulfonyl)aminomethyl}pyridin-2-ylamino) acetate or a salt thereof in the pharmaceutical composition is in a range of 0.001 to 0.003% (w/v), the content of the citric acid or the salt thereof is in a range of 0.1 to 0.2% (w/v), the content of the polyoxyethylene castor oil in the pharmaceutical composition is in a range of 0.1 to 3% (w/v), the content of the glycerin is in a range of 2.2 to 3% (w/v), the polyoxyethylene castor oil is not polyoxyethylene hardened castor oil, a number of polymerization of ethylene oxide of the polyoxyethylene castor oil is in a range of 5 to 100, and the pharmaceutical composition does not comprise sorbic acid.

2. The method according to claim 1, wherein the polyoxyethylene castor oil includes polyoxyethylene castor oil selected from the group consisting of polyoxyl 5 castor oil, polyoxyl 9 castor oil, polyoxyl 15 castor oil, polyoxyl 35 castor oil, and polyoxyl 40 castor oil.

3. The method according to claim 2, wherein the polyoxyethylene castor oil includes polyoxyl 35 castor oil.

4. The method according to claim 1, wherein the content of the polyoxyethylene castor oil in the pharmaceutical composition is in a range of 0.5 to 3% (w/v).

5. The method according to claim 4, wherein the content of the polyoxyethylene castor oil in the pharmaceutical composition is in a range of 0.8 to 2% (w/v).

6. The method according to claim 1, wherein the content of the polyoxyethylene castor oil in the pharmaceutical composition is in a range of 50 to 2,000 parts by mass relative to 1 part by mass of the isopropyl (6-{[4-(pyrazol-1-yl)benzyl](pyridin-3-ylsulfonyl)aminomethyl}pyridin-2-ylamino) acetate or a salt thereof.

7. The method according to claim 6, wherein the content of the polyoxyethylene castor oil in the pharmaceutical composition is in a range of 200 to 2,000 parts by mass relative to 1 part by mass of the isopropyl (6-{[4-(pyrazol-1-yl)benzyl](pyridin-3-ylsulfonyl)aminomethyl}pyridin-2-ylamino) acetate or a salt thereof.

8. The method according to claim 1, wherein the pharmaceutical composition further comprises edetic acid or a salt thereof.

9. The method according to claim 1, wherein the pharmaceutical composition is filled into a container made of polyethylene.

10. The method according to claim 1, wherein the pharmaceutical composition is for prevention or treatment of glaucoma or ocular hypertension, or for reduction of intraocular pressure.

* * * * *